US00PP18793P2

(12) United States Plant Patent
Trees

(10) Patent No.: US PP18,793 P2
(45) Date of Patent: May 6, 2008

(54) ***VERBENA* PLANT NAMED 'BALAZWHITIM'**

(50) Latin Name: *Verbena×hybrida*
Varietal Denomination: Balazwhitim

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/602,632

(22) Filed: Nov. 20, 2006

(51) Int. Cl.
*A01H 5/00* (2006.01)

(52) U.S. Cl. ..... Plt./308

(58) Field of Classification Search ..... Plt./308
See application file for complete search history.

(56) References Cited

PUBLICATIONS

Canada Plant Breeders' Rights application No. 06–5328 filed Mar. 9, 2006.
European Plant Breeders' Rights application No. 2006/2148 filed Oct. 27, 2006.

*Primary Examiner*—Anne Marie Grunberg
*Assistant Examiner*—June Hwu
(74) *Attorney, Agent, or Firm*—Audrey Charles

(57) ABSTRACT

A new and distinct cultivar of *Verbena* plant named 'Balazwhitim', characterized by its white-colored flowers, dark green-colored foliage, and moderately vigorous and trailing, spreading growth habit.

1 Drawing Sheet

Latin name of genus and species of plant claimed: *Verbena×hybrida.*
Variety denomination: 'Balazwhitim'.

BACKGROUND OF THE INVENTION

The present invention relates to a new and distinct cultivar of *Verbena* plant botanically known as *Verbena×hybrida* and hereinafter referred to by the cultivar name 'Balazwhitim'.

The new cultivar originated in a controlled breeding program in Arroyo Grande, Calif. during March 2003. The objective of the breeding program was the development of *Verbena* cultivars with unique flower coloration and a vigorous trailing, spreading growth habit.

The new *Verbena* cultivar was the result of a self-pollination of the proprietary *Verbena×hybrida* breeding selection designated BFP-1829-A, not patented, characterized by its pure white-colored flowers, dark green-colored foliage, and semi-trailing growth habit. The new cultivar was discovered and selected as a single flowering plant within the progeny of the above stated self-pollination during December 2003 in a controlled environment at Arroyo Grande, Calif.

Asexual reproduction of the new cultivar by terminal stem cuttings since December 2003 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balazwhitim' as a new and distinct cultivar of *Verbena* plant:

1. White-colored flowers;
2. Dark green-colored foliage; and

3. Moderately vigorous and trailing, spreading growth habit.

Plants of the new cultivar differ from plants of the parent primarily in growth habit.

Of the many commercially available *Verbena* cultivars known to the inventor, the most similar in comparison to the new cultivar is WILDFIRE White 'Balazwhit', U.S. Plant Pat. No. 13,943. However, in side by side comparisons, plants of the new cultivar differ from plants of 'Balazwhit' in the following characteristics:

1. Plants of the new cultivar are taller than plants of 'Balazwhit'; and
2. Plants of the new cultivar are narrower than plants of 'Balazwhit'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balazwhitim'. The plants were grown in 4.5 inch pots for 13 weeks in a greenhouse at West Chicago, Ill.

DETAILED BOTANICAL DESCRIPTION

Figure 1:
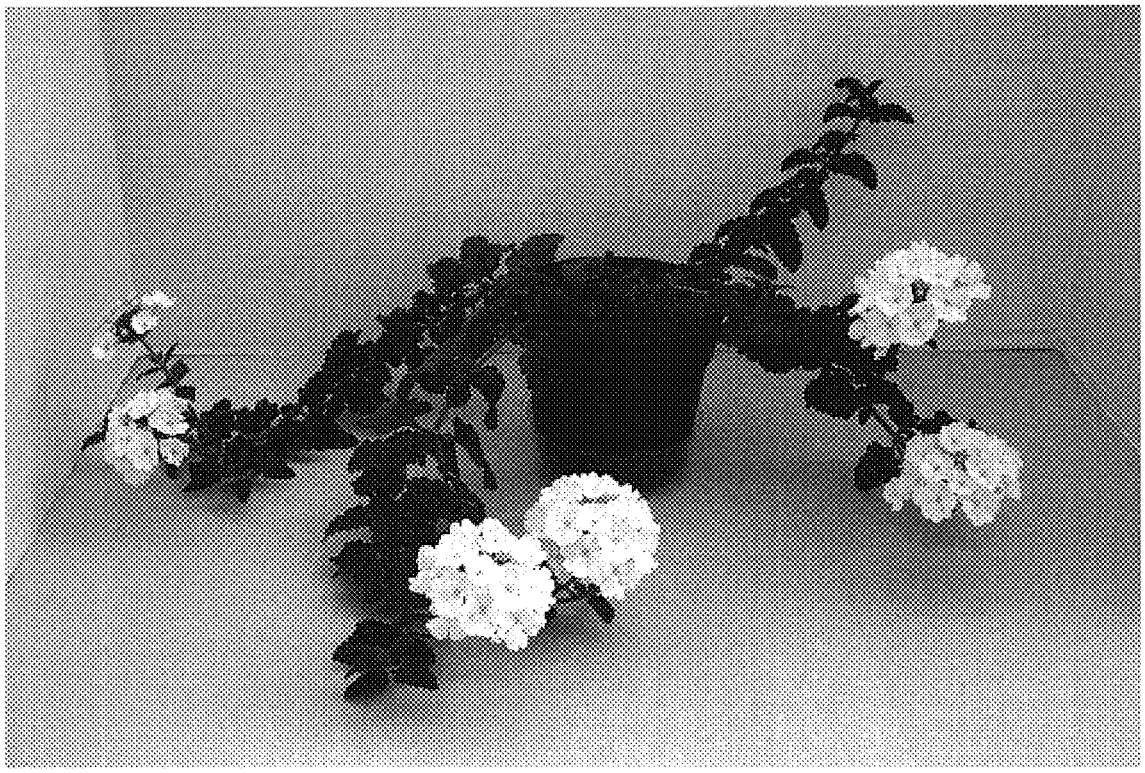
FIG. 1 illustrates a side view of the overall growth and flowering habit of 'Balazwhitim'.
Figure 2:
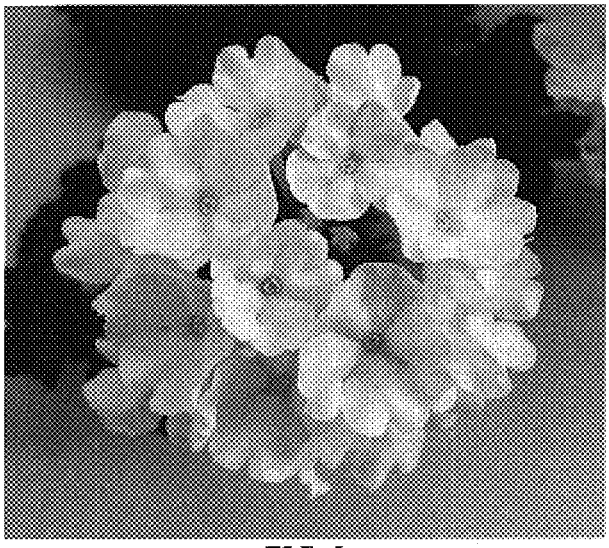
FIG. 2 illustrates a close-up view of an individual inflorescence of 'Balazwhitim'.
Figure 3:
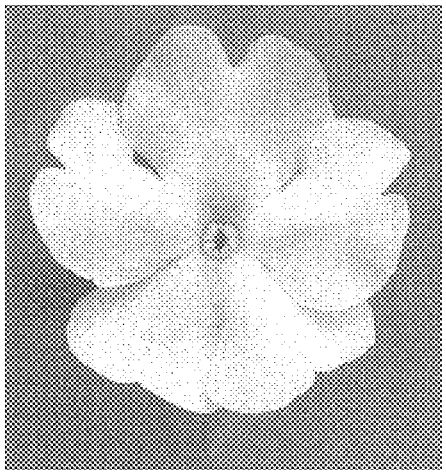
FIG. 3 illustrates a close-up view of an individual flower of 'Balazwhitim'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Feb. 28, 2006 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 13 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Verbena×hybrida* cultivar Balazwhitim.

Parentage:

*Parent.*—Proprietary *Verbena×Hybrida* breeding selection designated BFP-1829-A, not patented.

Propagation:

*Type cutting.*—Terminal stem.

*Time to initiate roots.*—Approximately 6 to 9 days.

*Time to produce a rooted cutting.*—Approximately 24 to 28 days.

*Root description.*—Fibrous.

*Rooting habit.*—Freely branching.

Plant description:

*Commercial crop time.*—Approximately 5 to 7 weeks from a rooted cutting.

*Growth habit and general appearance.*—Moderately vigorous and trailing, spreading.

*Size.*—Height from soil level to top of plant plane: Approximately 12.1 cm. Width: Approximately 50.0 cm.

*Branching habit.*—Freely branching. Quantity of main branches per plant: Approximately 5.

*Branch.*—Shape: Square in cross section. Strength: Strong. Length: Approximately 31.2 cm. Diameter: Approximately 2.6 mm. Length of central internode: Approximately 2.0 cm. Texture: Densely pubescent with a mixture of glandular and nonglandular hairs. Color of young and mature stems: 144A.

Foliage description:

*General description.*—Quantity of leaves per main branch: Approximately 25. Fragrance: None. Form: Simple. Arrangement: Opposite.

*Leaves.*—Aspect: Perpendicular to stem. Shape: Ovate. Margin: Lobed. Apex: Acute, turning obtuse with age. Base: Truncate. Venation pattern: Pinnate. Length of mature leaf: Approximately 4.6 cm. Width of mature leaf: Approximately 2.9 cm. Texture of upper surface: Densely pubescent. Texture of lower surface: Sparsely pubescent and densely glandular pubescent on veins. Color of upper surface of young foliage: 139A with venation of 144D. Color of lower surface of young and mature foliage: 138B with venation of 145C. Color of upper surface of mature foliage: 137A with venation of 144D.

*Petiole.*—Length: Approximately 7.0 mm. Diameter: Approximately 2.0 mm. Texture: Densely pubescent with a mixture of glandular and nonglandular hairs. Color: 144D.

Flowering description:

*Flowering habit.*—'Balazwhitim' is freely flowering under outdoor growing conditions with substantially continuous blooming from spring through autumn and year round in greenhouse environment.

*Lastingness of individual flower on the plant.*—Approximately 5 to 7 days.

Inflorescence description:

*General description.*—Type: Corymb. Quantity per plant: Approximately 4. Fragrance: None. Length or height: Approximately 5.9 cm. Width: Approximately 3.6 cm. Quantity of fully open flowers per inflorescence: Approximately 19.

*Peduncle.*—Strength: Strong. Aspect: Erect. Length: Approximately 4.7 cm. Diameter: Approximately 2.0 mm. Texture: Densely pubescent with a mixture of glandular and nonglandular hairs. Color: 144A.

Flower description:

*General description.*—Type: Sessile, salverform.

*Bud.*—Rate of opening: Generally takes 2 to 3 days for bud to progress from first color to fully open flower.

*Bud just before opening.*—Shape: Elongated. globular at apex. Length: Approximately 1.6 cm. Diameter: Approximately 3.9 mm. Color: 4D.

*Corolla.*—Shape: Round. Diameter: Approximately 2.1 cm. Depth: Approximately 2.3 cm.

*Petals.*—Quantity: 5, fused at base forming a tube. Shape: Obovate. Appearance: Velvety. Margin: Entire. Apex: Emarginate. Length of upper petal from tube: Approximately 1.1 cm. Width of upper petal: Approximately 1.2 cm. Length of lateral petals from tube: Approximately 1.1 cm. Width of lateral petals: Approximately 1.2 cm. Length of lower petals from tube: Approximately 9.5 mm. Width of lower petals: Approximately 1.0 cm. Texture of upper surface: Glabrous. Texture of lower surface of upper and lateral petals: Glabrous. Texture of lower surface of lower petals: Sparsely glandular pubescent. Color of upper surface when fully open: 155D with a base of 145B and 145C. Color of lower surface when fully open: 155D. Whisker color surrounding the opening of the corolla tube: 155C.

*Corolla tube.*—Length: Approximately 2.0 cm. Diameter of distal end: Approximately 2.0 mm. Diameter at proximal end: Approximately 1.5 mm. Texture of inner surface: Densely pubescent. Texture of outer surface: Sparsely glandular pubescent. Color of inner and outer surfaces: 145D at proximal end transitioning to 145C at distal end.

*Calyx.*—Shape: Tubular with 5 acute tips. Length: Approximately 1.2 cm. Width: Approximately 3.0 mm.

*Sepals.*—Quantity per flower: 5, fused at base. Shape: Linear. Apex: Acute. Length: Approximately 1.2 cm. Width: Approximately 1.0 mm. Texture: Densely pubescent with a mixture of glandular and nonglandular hairs. Gland color: Colorless. Color of upper and lower surfaces: 137A, transparent where margins fuse. Stipule shape: Lanceolate. Stipule apex: Acuminate. Stipule length: Approximately 8.2 mm. Stipule width at base: Approximately 2.0 mm. Stipule texture: Densely pubescent with a mixture of glandular and nonglandular hairs. Stipule gland color: Colorless. Stipule color: 144A at base transitioning to 137A at apex.

*Reproductive organs.*—Androecium: Stamen quantity: 4 per flower. Stamen length: Approximately 1.8 mm. Anther shape: Ovoid. Anther length: Approximately 1.0 mm. Anther color: 150B. Pollen amount: Moderate. Pollen color: 150D. Gynoecium: Pistil quantity: 1 per flower. Pistil length: Approximately 1.9 cm. Stigma shape: Biparted. Stigma length: Less than 1 mm. Stigma color: 143A. Style length: Approximately 1.7 cm. Style color: 144C transitioning to 144D at base. Ovary diameter: Approximately 1.5 mm. Ovary texture: Glabrous. Ovary color: 144B.

Seed and fruit production: Neither seed nor fruit production has been observed.

Disease and pest resistance: Resistance to pathogens and pests common to *Verbena* has not been observed.

What is claimed is:

1. A new and distinct cultivar of *Verbena* plant named 'Balazwhitim', substantially as herein shown and described.

* * * * *